United States Patent [19]
Dubroeucq et al.

[11] Patent Number: 5,663,204
[45] Date of Patent: Sep. 2, 1997

[54] UREIDOACETAMIDE DERIVATIVES, THEIR PREPARATION AND THE MEDICAMENTS CONTAINING THEM

[75] Inventors: Marie-Christine Dubroeucq, Enghien les Bains; Claude Guyon, Saint Maur des Fosses, both of France

[73] Assignee: Rhone-Poulenc Rorer S.A., Antony, France

[21] Appl. No.: 397,044
[22] PCT Filed: Sep. 6, 1993
[86] PCT No.: PCT/FR93/00847
    § 371 Date: Mar. 10, 1995
    § 102(e) Date: Mar. 10, 1995
[87] PCT Pub. No.: WO94/06825
    PCT Pub. Date: Mar. 31, 1994
[30] Foreign Application Priority Data
    Sep. 11, 1992 [FR] France ................. 92 10838
[51] Int. Cl.⁶ ................. A61K 31/17; C07C 309/02
[52] U.S. Cl. ................. 514/596; 562/41
[58] Field of Search ................. 564/49; 514/596; 562/37, 41

[56] References Cited

U.S. PATENT DOCUMENTS

| | | | |
|---|---|---|---|
| 5,223,529 | 6/1993 | Bourzat et al. | 514/414 |
| 5,382,590 | 1/1995 | Bourzat et al. | 514/396 |
| 5,475,106 | 12/1995 | Bourzat et al. | 544/58.4 |

FOREIGN PATENT DOCUMENTS

WO91/12264  8/1991  WIPO.

*Primary Examiner*—Joseph Conrad
*Attorney, Agent, or Firm*—Finnegan, Henderson, Farabow, Garrett & Dunner, L.L.P.

[57] ABSTRACT

This invention relates to compounds of formula (I), in which R denotes a hydrogen atom or a methoxy radical. The invention also concerns the salts of said compounds, their racemic forms, their enantiomers, the preparation of said derivatives and drugs containing same.

5 Claims, No Drawings

UREIDOACETAMIDE DERIVATIVES, THEIR PREPARATION AND THE MEDICAMENTS CONTAINING THEM

DESCRIPTION OF THE INVENTION

In Patent Applications WO 91/12264 and WO 91/13907, ureidoacetamide derivatives are described which are useful as cholecystokinin (CCK) and gastrin antagonists.

It has now been found that the compounds of formula:

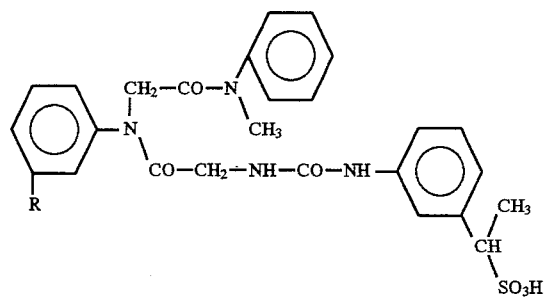

in which R represents a hydrogen atom or a methoxy radical, their salts, their racemates and their enantiomers unexpectedly have CCK antagonist properties which are much better than those of the ureidoacetamides of Patent Applications WO 91/12264 and WO 91/13907.

The subject of the present invention is thus the compounds of formula (I), their salts, their enantiomers, their preparation and the medicaments containing them.

The compounds of formula (I) can be prepared by reacting a derivative of formula:

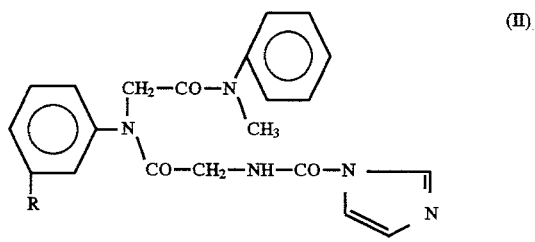

in which R represents a hydrogen atom or a methoxy radical, with an amine of formula:

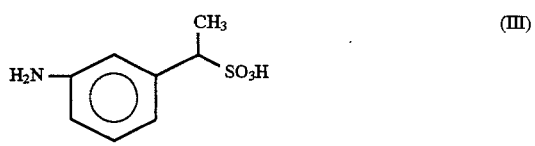

in the form of a salt.

This reaction is generally carried out in an inert solvent, such as benzene or toluene, at the boiling temperature of the reaction mixture. Tetraalkylammonium or trialkylphenylammonium salts, and preferably tetra-n-butylammonium salts, can be used as salts.

The derivatives of formula (II) can be obtained by application or adaptation of the methods described in the Patent Applications WO 91/12264 and WO 91/13907.

The enantiomers can be prepared from the chiral precursors of the compound of formula (III).

Preferably, the enantiomers are prepared from a tetraalkylammonium salt (Form B) of the amine of formula (III) or from the hydroquinine salt (Form A) of the amine of formula (III).

The compounds of formula (I) can be purified by the usual known methods, for example by crystallization, precipitation, chromatography or extraction.

The compounds of formula (I) and their enantiomers can be converted to metal salts or to addition salts with nitrogenous bases according to methods known per se. These salts can be obtained by reacting a metal base (alkali metal or alkaline-earth metal, for example), ammonia, an amine or a salt of an organic acid with a compound of formula (I) or its enantiomers, in a solvent.

As examples of pharmaceutically acceptable salts, there can be mentioned the salts with alkali metals (sodium, potassium, lithium) or with alkaline-earth metals (calcium, magnesium), the ammonium salt, or the salts of nitrogenous bases (ethanolamine, trimethylamine, methylamine, benzylamine, N-benzyl-β-phenethylamine, choline, arginine, leucine, lysine, N-methylglucamine).

The compounds of formula (I) and their enantiomers have advantageous pharmacological properties. These compounds have a strong affinity for cholecystokinin (CCK) and gastrin receptors and are thus useful in the treatment and prevention of disorders linked to CCK and to gastrin in the nervous system and the gastrointestinal system.

In this way, these compounds can be used for the treatment of the prevention of psychoses, of anxious disorders, of panic attacks, of Parkinson's disease, of tardive dyskinesia, of irritable bowel syndrome, of acute pancreatitis, of ulcers, of disorders of intestinal motility, of certain tumours sensitive to CCK, as an appetite regulator, in weaning from chronic treatments and alcohol or medicinal abuse, and as a pupil constrictor.

These compounds also have a potentiating effect on the analgesic activity of narcotic and non-narcotic medicaments. Additionally, they can have their own analgesic effect.

Moreover, the compounds having a high affinity for CCK receptors modify memorising abilities. Consequently, these compounds can be effective in memory disorders.

Affinity of the compounds of formula (I) for CCK receptors was determined according to a technique inspired by that of A. Saito et al. (J. Neuro. Chem., 37, 483–490 (1981) in the cerebral cortex.

In this test, the $IC_{50}$ of the compounds of formula (I) is less than 2 nM.

Moreover, it is known that the products which recognize the central receptors of CCK have a similar specificity for the receptors of gastrin in the gastrointestinal tract (Bock et al., J. Med. Chem., 32, 16–23 (1989); Reyfeld et al., Am. J. Physiol., 240, G 255–266 (1981); Beinfeld et al., Neuropeptides, 3, 411–427 (1983)).

The compounds of formula (I) have a low toxicity. Their subcutaneous $LD_{50}$ in mice is greater than 40 mg/kg.

The following compounds are particularly advantageous:

(RS)-1-{3-{3-[N-(3-Methoxyphenyl)-N-(N-methyl-N-phenylcarbamoylmethyl)carbamoylmethyl]ureido}-phenyl}ethanesulphonic acid (−)-1-{3-{3- [N-(3-Methoxyphenyl)-N-(N-methyl-N-phenylcarbamoylmethyl)carbamoylmethyl]ureido}-phenyl}ethanesulphonic acid (RS)-1-{3-{3-[N-(Methyl-N-phenylcarbamoylmethyl)-N-phenylcarbamoylmethyl]ureido}phenyl}-ethanesulphonic acid.

EXAMPLES

The following examples illustrate the invention without limiting it.

Example 1

6.7 g of tetra-n-butylammonium (RS)-1-(3-aminophenyl) ethanesulphonate are added to a solution of 5.5 g of 2-{2-

[(1-imidazolyl)carboxamido]-N-(3-methoxyphenyl) acetamido}-N-methyl-N-phenylacetamide in 120 cm³ of toluene. The reaction mixture is stirred at reflux for 5 hours and then concentrated to dryness under reduced pressure (2.7 kPa) at 45° C. The residue is dissolved in 200 cm³ of methylene chloride and the solution obtained is washed with 200 cm³ of a 2N aqueous hydrochloric acid solution and then with 2 times 200 cm³ of water. The organic phase is dried over magnesium sulphate and concentrated to dryness under reduced pressure (2.7 kPa) at 40° C. The crude product obtained is stirred for 30 minutes in 100 cm³ of diisopropyl ether. The insoluble product is separated by filtration and then dissolved in 20 cm³ of acetone. 3.0 g of potassium nonafluorobutanesulphonate in solution in 10 cm³ of acetone are added and then 25 cm³ of diisopropyl ether are added. The insoluble product is separated by filtration, washed with 2 times 5 cm³ of acetone and then 4 times 15 cm³ of diisopropyl ether and air-dried. There are thus obtained 5.5 g of potassium (RS)-1-{3-{3-[N-(3-methoxyphenyl)-N-(N-methyl-N-phenylcarbamoylmethyl) carbamoylmethyl]-ureido}phenyl}ethanesulphonate melting at approximately 180° C.

N.M.R. spectrum: (300 MHz; d6-DMSO): δ (ppm):

| | |
|---|---|
| 1.43 | [d, J = 7 Hz, 3H, —CH(C$\underline{H}_3$)—] |
| 3.18 | [broad s, 3H, —N(C$\underline{H}_3$)—] |
| 3.60 | [mt, 1H, —C$\underline{H}$(CH$_3$)—] |
| 3.65 | [broad d, J = 5 Hz, 2H, —CO(C$\underline{H}_2$)NH—] |
| 3.79 | [s, 3H, —OC$\underline{H}_3$] |
| 4.09 | [large, 2H, —CO(CH$_2$)N<] |
| 6.28 | [broad t, J = 5 Hz, 1H, —N$\underline{H}$—] |
| 6.86 | [d, J = 7.5 Hz, 1H, —C$_6$H$_4$(—H4) of the N-(3-methoxyphenyl)] |
| from 6.95 to 7.15 | [mt, 4H, aromatic protons] |
| 7.17 | [broad s, 1H, —C$_6$H$_4$(—H2) of the N-(3-methoxyphenyl)] |
| from 7.30 to 7.50 | [mt, 11H, aromatic protons] |
| 8.80 | [broad s, 1H, —CO—N$\underline{H}$—Ar]. |

Tetra-n-butylammonium (RS)-1-(3-aminophenyl)-ethanesulphonate can be prepared in the following way: 0.8 g of 5% palladium charcoal is added to a solution of 17.8 g of tetra-n-butylammonium (RS)-1-(3-nitrophenyl)ethanesulphonate in 200 cm³ of ethanol. The suspension is stirred for 3 hours at a temperature in the region of 25° C. under a hydrogen atmosphere (100 kPa). The catalyst is separated by filtration and the filtrate is concentrated to dryness under reduced pressure (2.7 kPa) at 40° C. There are thus obtained 16.7 g of tetra-n-butylammonium (RS)-1-(3-amino-phenyl)ethanesulphonate in the form of an oil used as is in subsequent syntheses.

Tetra-n-butylammonium (RS)-1-(3-nitrophenyl)-ethanesulphonate can be prepared in the following way: 25.3 g of (RS)-1-(1-bromoethyl)-3-nitrobenzene are added to a solution of 20.8 g of sodium sulphite in 260 cm³ of water. The reaction mixture is stirred at 80° C. for 5 hours, cooled to approximately 25° C. and run into 2.5 liters of a 0.5M aqueous potassium dihydrogenphosphate solution. 40 g of tetra-n-butylammonium hydrogensulphate are added. The mixture is extracted with 3 times 500 cm³ of methylene chloride. The combined organic phases are washed with 2 times 500 cm³ of water, dried over magnesium sulphate and concentrated to dryness under reduced pressure (2.7 kPa) at 40° C. There are thus obtained 51.4 g of tetra-n-butylammonium (RS)-1-(3-nitrophenyl)ethanesulphonate in the form of an oil used as is in subsequent syntheses.

(RS)-1-(1-Bromoethyl)-3-nitrobenzene can be prepared according to the method described by E. Felder et al., J. Med. Chem., 13, 559 (1970).

2-{2-[(1-Imidazolyl)carboxamido]-N-(3-methoxphenyl) acetamido}-N-methyl-N-phenylacetamide can be prepared in the following way: a solution of 3.1 g of 2-[2-amino-N-(3-methoxyphenyl)acetamido]-N-methyl-N-phenylacetamide in 30 cm³ of anhydrous tetrahydrofuran is added to a solution of 3.0 g of N,N'-carbonyldiimidazole in 30 cm³ of anhydrous tetrahydrofuran. The solution is stirred for 16 hours at a temperature in the region of 25° C. and then concentrated to dryness under reduced pressure (2.7 kPa) at 40° C. The residue is dissolved in 50 cm³ of ethyl acetate and the solution obtained is washed with 4 times 30 cm³ of water. The organic phase is dried over magnesium sulphate and then concentrated to dryness under reduced pressure (2.7 kPa) at 4° C. There are obtained, after recrystallisation from ethyl acetate, 3.5 g of 2-{2-[(1-imidazolyl) carboxamido]-N-(3-methoxyphenyl)acetamido}-N-methyl-N-phenylacetamide melting at 146° C.

2-[2-Amino-N-(3-methoxyphenyl)acetamido]-N-methyl-N-phenylacetamide can be prepared in the following way: 1.3 g of hydrazine hydrate are added to a solution of 3.5 g of 2-[N-(3-methoxyphenyl)-2-phthalimidoacetamido]-N-methyl-N-phenylacetamide in 60 cm³ of methanol. The reaction mixture is stirred at reflux for 30 minutes and then, after cooling, 100 cm³ of water are added. The mixture is concentrated to approximately 100 cm³, then brought to a pH of 9 with a 2N aqueous sodium hydroxide solution and extracted with 2 times 50 cm³ of ethyl acetate. The combined organic phases are washed with 2 times 50 cm³ of water, dried over magnesium sulphate and then concentrated to dryness under reduced pressure (2.7 kPa) at 40° C. There are thus obtained 3.0 g of 2-[2-amino-N-(3-methoxyphenyl) -acetamido]-N-methyl-N-phenylacetamide in the form of an oil used as is in subsequent syntheses.

2-[N-(3-Methoxyphenyl)-2-phthalimidoacetamido]-N-methyl-N-phenylacetamide can be prepared in the following way: 10 cm³ of dimethylformamide and then, over 1 hour, 30.2 g of oxalyl dichloride are added to a suspension of 80.6 g of 2-[N-(3-methoxyphenyl)-2-phthalimidoacetamido] acetic acid in 900 cm³ of 1,2-dichloroethane. The mixture is stirred for 2 hours at a temperature in the region of 25° C. and then 58.6 g of N-methylaniline are added over 45 minutes. The reaction mixture is stirred for 2 hours at a temperature in the region of 25° C., washed with 2 times 500 cm³ of water and then 300 cm³ of a saturated aqueous sodium hydrogencarbonate solution, dried over magnesium sulphate and concentrated to dryness under reduced pressure (2.7 kPa) at 40° C. The residue is stirred for 1 hour in 300 cm³ of diisopropyl ether, the insoluble product is separated by filtration, washed with 3 times 60 cm³ of diisopropyl ether and air-dried. There are thus obtained 84 g of 2-[N-(3-methoxyphenyl)-2-phthalimidoacetamido]-N-methyl-N-phenylacetamide melting at 137° C.

2-[N-(3-Methoxyphenyl)-2-phthalimidoacetamido]acetic acid can be prepared in the following way: 74.0 g of trifluoroacetic acid are added to a solution of 42.0 g of tert-butyl 2-[N-(3-methoxyphenyl)-2-phthalimidoacetamido]acetate in 500 cm³ of methylene chloride. The solution obtained is stirred at reflux for 5 hours and then concentrated to dryness under reduced pressure (2.7 kPa) at 40° C. The residue is stirred for 1 hour in 100 cm³ of diisopropyl ether, the insoluble product is separated by filtration, washed with 3 times 40 cm³ of diisopropyl ether and air-dried. There are thus obtained 36 g of 2-[N-(3-methoxyphenyl)-2-phthalimidoacetamido]acetic acid melting at 203° C.

tert-Butyl 2-[N-(3-methoxyphenyl)-2-phthalimidoacetamido]acetate can be prepared in the following way: 14.9 g of an oily suspension (60% by weight) of sodium hydride are added over 30 minutes to a solution of 96 g of N-(3-methoxyphenyl)-2-phthalimidoacetamide in 1000 cm$^3$ of anhydrous tetrahydrofuran. The suspension is stirred for 4 hours at a temperature in the region of 20° C. and then 72.7 g of tert-butyl bromoacetate are added over 15 minutes. The reaction mixture is stirred for 16 hours at a temperature in the region of 25° C., slowly hydrolyzed with 50 cm$^3$ of water and then concentrated to dryness under reduced pressure. The residue obtained is stirred for 1 hour in 400 cm$^3$ of water, the insoluble product is separated by filtration, washed with 3 times 100 cm$^3$ of water, 2 times 100 cm$^3$ of diisopropyl ether and air-dried. There are thus obtained 82.0 g of tert-butyl 2-[N-(3-methoxyphenyl)-2-phthalimidoacetamido]acetate melting at 148° C.

N-(3-Methoxyphenyl)-2-phthalimidoacetamide can be prepared in the following way: 22.0 g of triethylamine and then 48.0 g of 2-phthalimidoacetyl chloride in solution in 300 cm$^3$ of methylene chloride are added to a solution of 26.0 g of 3-methoxyaniline in 200 cm$^3$ of methylene chloride while maintaining the temperature at approximately 20° C. The reaction mixture is stirred for 4 hours at this temperature and then 800 cm$^3$ of water are added. The insoluble product is separated by filtration, washed with 3 times 100 cm$^3$ of water and air-dried. There are thus obtained 65.0 g of N-(3-methoxyphenyl)-2-phthalimidoacetamide melting at 171° C.

2-Phthalimidoacetyl chloride can be prepared according to the method described by W. Grassmann and E. Schulte-Uebbing, Chem. Bet., 83, 244–247, (1950).

Example 2

2.7 g of tetra-n-butylammonium 1-(3-aminophenyl)ethanesulphonate, form B, are added to a solution of 2.1 g of 2-{2-[(1-imidazolyl)carboxamido]-N-(3-methoxyphenyl)acetamido}-N-methyl-N-phenylacetamide in 130 cm$^3$ of toluene. The reaction mixture is stirred at reflux for 5 hours and then concentrated to dryness under reduced pressure (2.7 kPa) at 45° C. The residue is dissolved in 100 cm$^3$ of methylene chloride and the solution obtained is washed with 50 cm$^3$ of a 2N aqueous hydrochloric acid solution and then with 2 times 50 cm$^3$ of water. The organic phase is dried over magnesium sulphate and concentrated to dryness under reduced pressure (2.7 kPa) at 40° C. The crude product obtained is stirred for 30 minutes in 50 cm$^3$ of diisopropyl ether. The insoluble product is separated by filtration and then dissolved in 6 cm$^3$ of acetone. 1.2 g of potassium nonafluorobutanesulphonate in solution in 3 cm$^3$ of acetone are added and then 5 cm$^3$ of diisopropyl ether are added. The insoluble gum is separated and then stirred for 1 hour in 12 cm$^3$ of an acetone and diisopropyl ether mixture (50/50 by volume). The insoluble product is separated by filtration, washed with 2 times 5 cm$^3$ of an acetone and diisopropyl ether mixture (50/50 by volume) and then with 4 times 5 cm$^3$ of diisopropyl ether, and air-dried. There are thus obtained 1.55 g of potassium (−)-1-{3-{3-[N-(3-methoxyphenyl)-N-(N-methyl-N-phenylcarbamoylmethyl) carbamoylmethyl] ureido}phenyl}ethanesulphonate melting at approximately 180° C.

$[\alpha]_D^{20} = -5.0° \pm 0.5$ (c=0.888%, methanol)

N.M.R. spectrum: (300 MHz; d6-DMSO: (−)-form) d(ppm):

| 1.43 | [d, J = 7 Hz, 3H, —CH(C$\underline{H}_3$)—] |
|---|---|
| 3.18 | [broad s, 3H, —N(C$\underline{H}_3$)—] |
| 3.60 | [mt, 1H, —C$\underline{H}$(CH$_3$)—] |
| 3.65 | [broad d, J = 5 Hz, 2H, —CO(C$\underline{H}_2$)NH—] |
| 3.79 | [s, 3H, —OC$\underline{H}_3$] |
| 4.09 | [large, 2H, —CO(CH$_2$)N<] |
| 6.28 | [broad t, J = 5 Hz, 1H, —N$\underline{H}$—] |
| 6.86 | [d, J = 7.5 Hz, 1H, —C$_6$H$_4$(—H4) of the N-(3-methoxyphenyl)] |
| from 6.95 to 7.15 | [mt, 4H, aromatic protons] |
| 7.17 | [broad s, 1H, —C$_6$H$_4$(—H2) of the N-(3-methoxyphenyl)] |
| from 7.30 to 7.50 | [mt, 11H, aromatic protons] |
| 8.80 | [broad s, 1H, —CO—N$\underline{H}$—Ar]. | tetra-n-Butylammonium 1-(3-aminophenyl)ethanesulphonate, form B, can be prepared in the following way: 0.2 g of 5 % palladium charcoal is added to a solution of 2.8 g of tetra-n-butylammonium 1-(3-nitrophenyl)ethanesulphonate, form B, in 50 cm$^3$ of ethanol. The suspension is stirred for 2 hours at a temperature in the region of 25° C. under a hydrogen atmosphere (100 kPa). The catalyst is separated by filtration and the filtrate is concentrated to dryness under reduced pressure (2.7 kPa) at 40° C. There are thus obtained 2.8 g of tetra-n-butylammonium 1-(3-aminophenyl)ethanesulphonate, form B, in the form of an oil used as is in subsequent syntheses.

tetra-n-Butylammonium 1-(3-nitrophenyl)ethanesulphonate, form B, can be prepared in the following way: 5.2 g of potassium nonafluorobutanesulphonate in solution in 12 cm$^3$ of acetone are added to a solution of 10.5 g of N-benzylquininium 1-(3-nitrophenyl)ethanesulphonate, a mixture of forms A and B (approximately 15/85 in moles), in 16 cm$^3$ of acetone. The insoluble product is separated by filtration and then dissolved in 9 cm$^3$ of water. 8.4 cm$^3$ of a 1N aqueous hydrochloric acid solution and 1.15 g of R-(−)-phenylglycinol are added. The solution obtained is concentrated to dryness under reduced pressure (2.7 kPa) at 50° C. The residue obtained is extracted with 3 times 15 cm$^3$ of acetonitrile at reflux. The organic phases are combined and concentrated to approximately 7 cm$^3$; after cooling, the crystals are separated by filtration and dissolved in 7.5 cm$^3$ of a 1N aqueous sodium hydroxide solution. The solution obtained is washed with 8 times 25 cm$^3$ of diethyl ether and then 60 cm$^3$ of a 0.5M aqueous potassium dihydrogenphosphate solution and 2.3 g of tetra-n-butylammonium hydrogensulphate are added. The mixture is extracted with 3 times 30 cm$^3$ of methylene chloride. The combined organic phases are dried over magnesium sulphate and concentrated to dryness under reduced pressure (2.7 kPa) at 40° C. There are thus obtained 2.8 g of tetra-n-butylammonium 1-(3-nitrophenyl)ethanesulphonate, form B, in the form of an oil used as is in subsequent syntheses.

N-Benzylquininium 1-(3-nitrophenyl)ethanesulphonate, a mixture of forms A and B, can be prepared in the following way: 87 g of potassium dihydrogenphosphate and 32.4 g of N-benzylquininium chloride are added to a solution of 17.2 g of potassium (RS)-1-(3-nitrophenyl)ethanesulphonate in 400 cm$^3$ of water. The mixture is extracted with 2 times 300 cm$^3$ of methylene chloride. The combined organic phases are washed with 2 times 200 cm³ of water, dried over magnesium sulphate and concentrated to dryness under reduced pressure (2.7 kPa) at 40° C. The foam obtained is dissolved in 120 cm³ of 2-propanol at reflux. After cooling, the crystals are separated by filtration and washed with 2 times 15 cm³ of 2-propanol. There are obtained, after 2 recrystallizations from 350 and 500 cm³ of 2-propanol, 15.6 g of N-benzylquininium 1-(3-nitrophenyl)ethanesulphonate, form A, melting at approximately 110° C. $[\alpha]_D^{20} = -151.3° \pm 1.5$ (c=1.009%; Methanol). The propanol solutions are combined and concentrated to dryness under reduced pressure (2.7 kPa) at 45° C. There are thus obtained 25.0 g of N-benzylquininium 1-(3-nitrophenyl)-ethanesulphonate, a mixture of forms A and B (approximately 15/85 in moles).

Potassium (RS)-1-(3-nitrophenyl)ethanesulphonate can be prepared in the following way: 25.3 g of (RS)-1-(1-bromoethyl)-3-nitrobenzene are added to a solution of 20.8 g of sodium sulphite in 260 cm³ of water. The reaction mixture is stirred at 80° C. for 5 hours, cooled to approximately 25° C. and run into 2.5 liters of a 0.5M aqueous potassium dihydrogenphosphate solution. 40 g of tetra-n-butylammonium hydrogensulphate are added. The mixture is extracted with 3 times 500 cm³ of methylene chloride. The organic phases are washed with 2 times 500 cm³ of water, dried over magnesium sulphate, and concentrated to dryness under reduced pressure (2.7 kPa) at 40° C. The oil obtained is dissolved in 65 cm³ of acetone and 34 g of potassium nonafluorobutanesulphonate in solution in 75 cm³ of acetone are added. The insoluble product is separated by filtration, washed with 3 times 50 cm³ of diisopropyl ether and air-dried. There are thus obtained 22.4 g of potassium (RS)-1-(3-nitrophenyl)ethanesulphonate, melting at a temperature greater than 260° C. and used as is in subsequent syntheses.

(RS)-1-(1-Bromoethyl)-3-nitrobenzene can be prepared according to the method described by E. Felder et al., J. Med. Chem., 13, 559 (1970).

Example 3

6.7 g of tetra-n-butylammonium (RS)-1-(3-aminophenyl)ethanesulphonate are added to a solution of 2.8 g of 2-{2-(1-imidazolyl)carboxamido]-N-phenyl-acetamido]-N-methyl-N-phenylacetamide in 70 cm³ of toluene. The reaction mixture is stirred at reflux for 5 hours and then concentrated to dryness under reduced pressure (2.7 kPa) at 45° C. The residue is dissolved in 100 cm³ of methylene chloride and the solution obtained is washed with 100 cm³ of a 2N aqueous hydrochloric acid solution and then with 2 times 100 cm³ of water. The organic phase is dried over magnesium sulphate and concentrated to dryness under reduced pressure (2.7 kPa) at 40° C. The crude product obtained is stirred for 30 minutes in 60 cm³ of diisopropyl ether. The insoluble product is separated by filtration and then dissolved in 20 cm³ of acetone. 1.9 g of potassium nonafluorobutanesulphonate in solution in 10 cm³ of acetone are added. The insoluble product is separated by filtration, washed with 4 times 5 cm³ of acetone and then 4 times 8 cm³ of diisopropyl ether and air-dried. There are thus obtained 5.5 g of potassium (RS)-1-{3-[3-(N-(N-methyl-N-phenylcarbamoylmethyl)-N-phenyl-carbamoylmethyl]ureido}phenyl)ethanesulphonate melting at approximately 210° C.

2-{2-[(1-Imidazolyl)carboxamido}-N-phenylacetamido}-N-methyl-N-phenylacetamide can be prepared in the following way: a solution of 37 g of 2-(2-amino-N-phenylacetamido)-N-methylacetamide in 150 cm³ of anhydrous tetrahydrofuran is added to a solution of 31 g of N,N'-carbonyldiimidazole in 300 cm³ of anhydrous tetrahydrofuran. The solution is stirred for 3 hours at a temperature in the region of 25° C. and then concentrated to dryness under reduced pressure (2.7 kPa) at 40° C. The residue is dissolved in 500 cm³ of ethyl acetate and the solution obtained is washed successively with 4 times 300 cm³ of distilled water and with 300 cm³ of a saturated aqueous sodium chloride solution. The organic phase is dried over magnesium sulphate and then concentrated to dryness under reduced pressure (2.7 kPa) at 40° C. There are obtained, after recrystallization from ethyl acetate, 33.3 g of 2-{2-[(1-imidazolyl)carboxamido}-N-phenylacetamido}-N-methyl-N-phenylacetamide melting at 120° C.

2-(2-Amino-N-phenylacetamido)-N-methyl-N-phenylacetamide can be prepared in the following way: 0.25 g of hydrazine hydrate is added to a solution of 1.4 g of N-methyl-N-phenyl-2-(N-phenyl-2-phthalimidoacetamido)acetamide in 15 cm³ of methanol. The reaction mixture is stirred at reflux for 2 hours. After cooling and addition of 5 cm³ of a 4N aqueous hydrochloric acid solution, the insoluble product is separated by filtration. The filtrate is concentrated to dryness under reduced pressure (2.7 kPa)) 30° C. The residue obtained is dissolved in 10 cm³ of distilled water and then the solution obtained is washed with 10 cm³ of diethyl ether, basified with 0.5 g of sodium hydroxide pellets and extracted with 2 times 20 cm³ of ethyl acetate. The combined organic phases are dried over magnesium sulphate and then concentrated to dryness under reduced pressure (2.7 kPa) at 30° C. There is thus obtained 0.9 g of 2-(2-amino-N-phenylacetamido)-N-methyl-N-phenylacetamide in the form of an oil used as is in subsequent syntheses.

N-Methyl-N-phenyl-2-(N-phenyl-2-phthalimidoacetamido)acetamide can be prepared in the following way: 3.9 g of oxalyl dichloride and then one drop of dimethylformamide are added to a suspension of 10.1 g of 2-(N-phenyl-2-phthalimidoacetamido)acetic acid in 125 cm³ of 1,2-dichloroethane. The mixture is stirred for 2 hours at a temperature in the region of 25° C. and then 7.7 g of N-methylaniline in solution in 30 cm³ of 1,2-dichloroethane are added. The solution obtained is stirred for 2 hours at a temperature in the region of 25° C. and then washed with 2 times 80 cm³ of distilled water, dried over magnesium sulphate and concentrated to dryness under reduced pressure (2.7 kPa) at 40° C. There are obtained, after recrystallization from diisopropyl ether, 9.6 g of N-methyl-N-phenyl-2-(N-phenyl-2-phthalimidoacetamido)acetamide melting at 216° C.

2-(N-Phenyl-2-phthalimidoacetamido)acetic acid can be prepared in the following way: 17.9 g of trifluoroacetic acid are added to a solution of 8 g of tert-butyl 2-(N-phenyl-2-phthalimidoacetamido)acetate in 30 cm³ of dichloromethane. The solution obtained is stirred at reflux for 1 hour and then concentrated to dryness under reduced pressure (2.7 kPa) at 40° C. There are obtained, after recrystallization from diisopropyl ether, 5.9 g of 2-(N-phenyl-2-phthalimidoacetamido)-acetic acid melting at 224° C.

tert-Butyl 2-(N-phenyl-2-phthalimidoacetamido)acetate can be prepared in the following way: 92.4 g of sodium hydrogen carbonate are added to a solution of 207 g of tert-butyl N-phenylglycinate in 500 cm³ of 1,2-dichloroethane. The suspension is stirred at a temperature in the region of 5° C. and a solution of 223 g of 2-phthalimidoacetyl chloride in 1100 cm³ of 1,2-dichloroethane is added. The reaction mixture is stirred at reflux for 4 hours. After separation of the insoluble product by filtration, the filtrate is washed with 300 cm³ of distilled water, dried over magnesium sulphate and concentrated to dryness under reduced pressure (2.7 kPa) at 40° C. There are obtained, after recrystallization from acetonitrile, 236 g of tert-butyl 2-(N-phenyl-2-phthalimidoacetamido)acetate melting at 128° C.

tert-Butyl N-phenylglycinate can be prepared in the following way: 58 g of tert-butyl bromoacetate are added to a solution of 56 g of aniline in 600 cm³ of 1,2-dichloroethane and the solution obtained is stirred at reflux for 48 hours. After cooling, the insoluble product is separated by filtration and the filtrate is washed with 200 cm³ of a 0.1N aqueous hydrochloric acid solution and with 3 times 200 cm³ of distilled water. The organic phase is dried over magnesium sulphate and then concentrated to dryness under reduced pressure (2.7 kPa) at 40° C. There are thus obtained 54 g of tert-butyl N-phenylglycinate in the form of an oil used as is in subsequent syntheses.

2-Phthalimidoacetyl chloride can be prepared according to the method described by W. Grassman and E. Schulte-Uebling, Chem. Ber., 83, 244 (1950).

The medicaments according to the invention consist of a compound of formula (I) in the free form or in the form of an addition salt with a pharmaceutically acceptable acid, in the pure state or in the form of a composition in which it is combined with any other pharmaceutically compatible product, which can be inert or physiologically active. The medicaments according to the invention can be used orally, parenterally, rectally or topically.

Tablets, pills, powders (gelatin capsules or cachets), or granules can be used as solid compositions for oral administration. In these compositions, the active principle according to the invention is mixed with one or a number of inert diluents, such as starch, cellulose, sucrose, lactose or silica, under an argon stream. These compositions can also comprise substances other than the diluents, for example one or a number of lubricating agents such as magnesium stearate or talc, a colouring agent, a coating agent (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavouring or stabilizing substances.

The sterile compositions for parenteral administration can preferably be aqueous solutions or non-aqueous solutions, suspensions or emulsions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eye drops, mouthwashes, nose drops or aerosols.

In human therapeutics, the compounds according to the invention are particularly useful in the treatment and prevention of disorders linked to CCK and to gastrin in the nervous system and the gastrointestinal system. These compounds can thus be used in the treatment and prevention of psychoses, anxious disorders, of panic attacks, of Parkinson's disease, of tardive dyskinesia, of irritable bowel syndrome, of acute pancreatitis, of ulcers, of disorders of intestinal motility, of certain tumours sensitive to CCK, of memory disorders, as analgesics, as potentiation agents of the analgesic activity of narcotic and non-narcotic analgesic medicaments and as an appetite regulator, in weaning from chronic treatments and alcohol or medicinal abuse and as a constrictor of the pupil of the iris of the eye.

The doses depend on the desired effect, on the duration of treatment and on the administration route used; they are generally between 0.05 g and 1 g per day orally for an adult with unit doses ranging from 10 mg to 500 mg of active substance.

Generally, the doctor will determine the appropriate dosage depending on the age, weight and all the other factors specific to the subject to be treated.

The following examples illustrate compositions according to the invention:

Example A

Gelatin capsules containing 50 mg of active product are prepared, according to the usual technique, which have the following composition:

| | |
|---|---|
| Potassium (RS)-1-{3-{3-[N-(3-methoxyphenyl)-N-(N-methyl-N-phenylcarbamoyl-methyl)carbamoylmethyl]ureido}phenyl}-ethanesulphonate | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

Example B

Tablets containing 50 mg of active product are prepared, according to the usual technique, which have the following composition:

| | |
|---|---|
| Potassium (−)-1-{3-{3-[(N-(3-methoxyphenyl)-N-(N-methyl-N-phenylcarbamoyl-methyl)carbamoylmethyl]ureido}phenyl}-ethanesulphonate | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) q.s. for one coated tablet completed to 245 mg | |

Example C

An injectable solution containing 10 mg of active product is prepared which has the following composition:

| | |
|---|---|
| Potassium (RS)-1-{3-{3-[N-(n-methyl-N-phenylcarbamoylmethyl)-N-phenylcarbamoyl-methyl]ureido}phenyl}ethanesulphonate | 10 mg |
| Benzoic acid | 80 mg |
| Benzyl alcohol | 0.06 cm³ |
| Sodium benzoate | 80 mg |
| 95% Ethanol | 0.4 cm³ |
| Sodium hydroxide | 24 mg |
| Propylene glycol | 1.6 cm³ |
| Water q.s. for | 4 cm³ |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Compounds of formula:

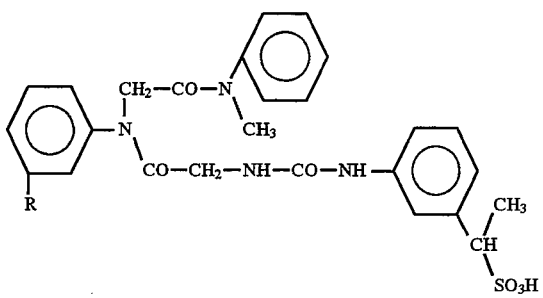
(I)

in which R represents a hydrogen atom or a methoxy radical, their salts, their racemates and their enantiomers.

2. Medicaments comprising, as active principle, at least one compound of formula (I) according to claim 1.

3. Medicaments according to claim 2 which are inhibitors of CCK and of gastrin.

4. The following compounds:

(RS)-1-{3-{3-[N-(3-Methoxyphenyl)-N-(N-methyl-N-phenylcarbamoylmethyl)carbamoylmethyl]ureido}-phenyl}ethanesulphonic acid (−)-1-{3-{3-[N-(3-Methoxyphenyl)-N-(N-methyl-N-phenylcarbamoylmethyl)carbamoylmethyl]ureido}-phenyl}ethanesulphonic acid (RS)-1-{3-{3-[N-(N-Methyl-N-phenylcarbamoylmethyl)-N-phenylcarbamoylmethyl]ureido}phenyl}-ethanesulphonic acid and their salts.

5. Process for preparing the compounds of formula (I)

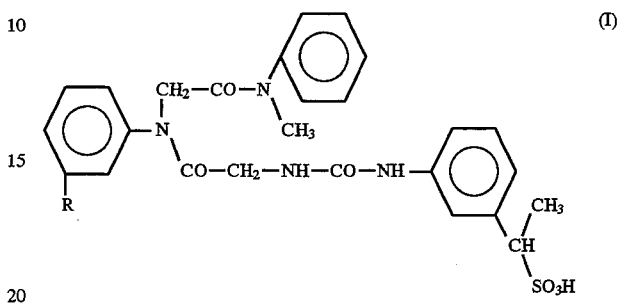
(I)

comprising reacting a derivative of formula:

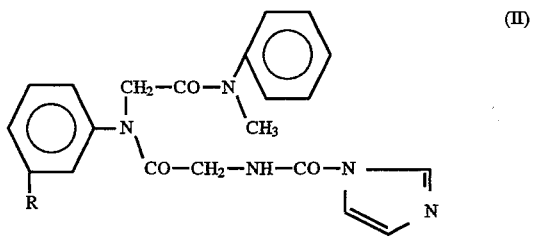
(II)

in which R represents a hydrogen atom or a methoxy radical, with an amine of formula:

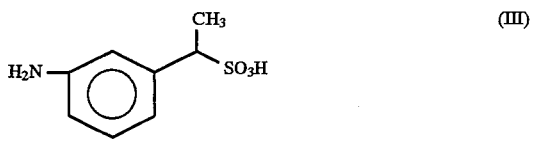
(III)

in the form of a salt and optionally in the form of an enantiomer, isolating the product and optionally converting to a salt and/or separating the enantiomers.

* * * * *